(12) United States Patent
Paldus et al.

(10) Patent No.: US 6,377,350 B1
(45) Date of Patent: Apr. 23, 2002

(54) FREQUENCY SEQUENCING USING CRDS

(75) Inventors: Barbara A. Paldus, Sunnyvale; Charles Harb, Palo Alto, both of CA (US)

(73) Assignee: Informal Diagnostics, Inc, Sunnyvale, CA (US)

( * ) Notice: Subject to any disclaimer, the term of this patent is extended or adjusted under 35 U.S.C. 154(b) by 0 days.

(21) Appl. No.: 09/497,333

(22) Filed: Feb. 3, 2000

(51) Int. Cl.[7] .................................................. G01B 9/02
(52) U.S. Cl. ........................................ 356/454; 356/519
(58) Field of Search .................................. 356/451, 454, 356/519, 437, 440

(56) References Cited

U.S. PATENT DOCUMENTS

| | | | | |
|---|---|---|---|---|
| 4,324,475 A | * | 4/1982 | Purdie | 356/519 |
| 4,455,089 A | * | 6/1984 | Yeung et al. | 356/454 |
| 5,903,358 A | * | 5/1999 | Zare et al. | 356/437 |
| 6,094,267 A | * | 7/2000 | Levenson et al. | 356/453 |

* cited by examiner

*Primary Examiner*—Samuel A. Turner
(74) *Attorney, Agent, or Firm*—John Schipper

(57) ABSTRACT

Method and system for generating a sequence of two or more light beam central frequencies. A first mirror, in an optical cavity defined by two or more mirrors, is moved to a sequence of two or more locations relative to a second mirror in the cavity. The first mirror location is dithered relative to the second mirror for each location in the sequence to produce a light beam having a dithered sequence of cavity frequencies that are related to longitudinal mode resonant frequencies for the cavity. Alternatively, frequency locking is implemented for each of the sequence of central frequencies. The light beam may be passed through a sample within the cavity for spectroscopic measurements or may be extracted from an empty cavity to provide a sequence of light beam frequencies for a subsequent application.

19 Claims, 6 Drawing Sheets

FREQUENCY SEQUENCING USING CRDS

FIELD OF THE INVENTION

This invention relates to provision of selected sequences of frequencies for spectroscopic analysis or other purposes.

BACKGROUND OF THE INVENTION

Cavity ring down spectroscopy (CRDS) is a laser-based, high sensitivity, absorption measurement technique that has become competitive with alternative techniques, such as intra-cavity laser absorption spectroscopy, frequency modulation spectroscopy, multipass spectroscopy and photoacoustic spectroscopy, for performing spectroscopic analysis of a sample. CRDS exploits the properties of a high finesse optical resonator, usually formed by two or more high reflectivity mirrors defining an optical cavity, with a sample located in the optical cavity. A narrow bandwidth laser light beam is injected into the optical resonator and abruptly terminated. The resulting rate of decay, R, of light beam intensity is measured and is linearly related to the optical resonator losses by a relation $$R = 1/\tau = L_{tot}/\Delta t_{rt}, \quad (1)$$

$$L_{tot} = L(\text{ref1}) + L(\text{sample}). \quad (2)$$

Here $\tau$ is the ring down decay constant (sec), $\Delta t_{rt}$ is the optical cavity round trip time, and $L(\text{ref1})$ and $L(\text{sample})$ are measures of the light beam intensity losses due to the resonator alone (no sample present) and due to sample absorption and scattering, respectively, at the chosen frequency.

Where a sample is to be analyzed using CRDS, a light beam at each of a sequence of two or more frequencies should be provided, in order to adequately characterize the sample by its absorption spectrum or transmission spectrum. In a conventional approach, in order to vary the round trip distance of a light beam within an optical cavity, the cavity is partially disassembled and reassembled by moving and realigning at least one mirror that defines the cavity. This approach is time consuming and inefficient and often does not provide the control needed to accurately provide a pre-selected sequence of resonance frequencies.

What is needed is a technique for providing a sequence of selected central frequencies of a light beam with a narrow frequency bandas measured by the full width at half maximum (FWHM), as an integral part of an optical system used for spectroscopic analysis of materials. Preferably, the technique should be flexible enough to allow provision of a sequence with uniformly spaced frequencies and/or of a sequence with arbitrarily spaced frequencies and should allow the chosen sequence to be stepped through without extensive reconstruction of the optical system. Preferably, the technique should be optically efficient so that substantially all light provided for the optical system is utilized in providing the sequence of light beam frequencies. Preferably, the frequency sequence should be available for use in CRDS analysis or for use in some other process that relies upon a light beam having a sequence of selectable frequencies.

SUMMARY OF THE INVENTION

These needs are met by the invention, which uses a cavity ring down approach with a rapidly reconfigurable optical cavity to generate a selected sequence of frequencies within the cavity itself. The distance between a line segment joining two mirrors that form part of the cavity, and a third mirror is varied, by moving the third mirror by a controllable amount. This controllable distance increment is chosen to provide a cavity round trip distance that defines a sequence of two or more selected resonance frequencies. The sequence of selected frequencies can be used to perform CRDS analysis of a sample within the cavity, or to provide a sequence of light beam frequencies external to the cavity for some process that is frequency-dependent.

BRIEF DESCRIPTION OF THE DRAWINGS

FIGS. 3 and 7 illustrate variation of a light beam round trip distance according to the invention.

DESCRIPTION OF BEST MODES OF THE INVENTION

Figure 1:
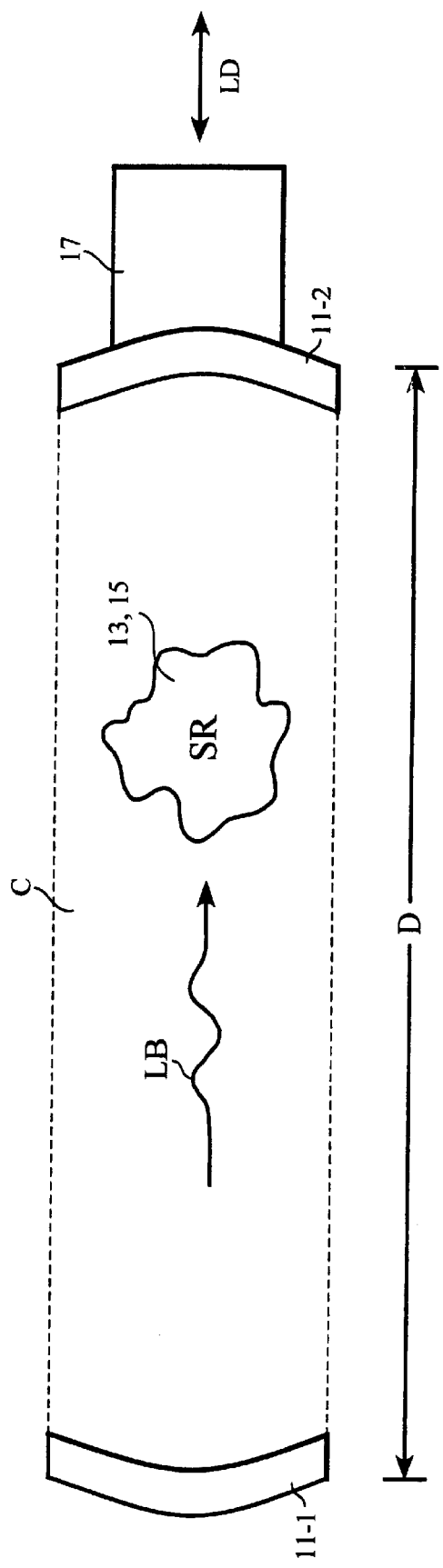
FIGS. 1 and 2 are schematic views of embodiments of apparatus for practicing the invention.
Figure 2:
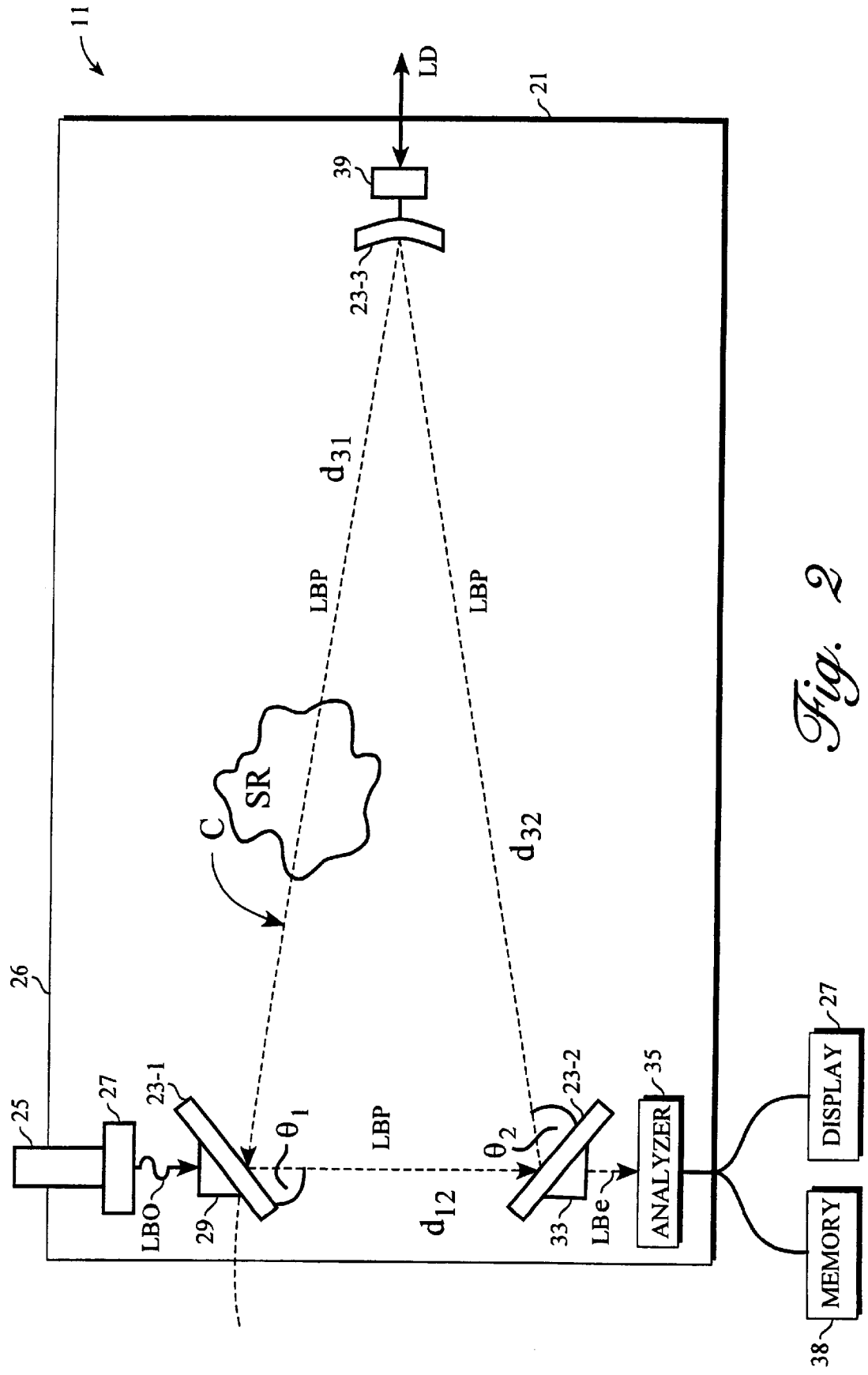

An embodiment for providing a selected sequence of frequencies according to the invention is illustrated in FIG. 1, where an optical resonator is formed by two highly reflecting mirrors, 11-1 and 11-2. Alternatively, the resonator may have a ring configuration and include two or more highly reflecting mirrors, such as 23-1, 23-2 and 23-3, as shown in FIG. 2. For a given mirror separation, $d_{12}$, mirror curvatures, r1 and r2, and mirror reflectivities, R1 and R2, certain resonator geometries will be optically stable, allowing a properly directed light beam to execute an numerous round trips within the cavity defined by the mirrors. For such an optically stable configuration, certain light beam wavelengths $\lambda$, determined with reference to the round trip distance $2 \cdot d_{12}$ and to the refractive index $n_{ref}$ of a medium located between the mirrors, 31-3 and 31-2, will support development of an optical resonator mode, longitudinal or transverse. A longitudinal mode wavelength $\lambda$ is determined by a phase round trip condition, such as $$\Delta \phi = 4\pi f \cdot d_{12} n_{ref}/\lambda + 4\pi(1-f) \cdot d_{12}/\lambda = 2\pi \cdot N (N=1,2,3,\dots), \quad (3)$$

where f is the fraction of the mirror-to-mirror path that is occupied by the sample. A transverse mode wavelength $\lambda$ is determined with reference to the effects of mirror geometry and mirror size on light beam diffraction within the optical cavity. Resonator stability conditions and resonator mode wavelengths are discussed in A. Yariv, *Optical Electronics*, Holt, Rinehart and Winston, New York, Third Edition, 1986, pp. 17–22, 87–120.

The ring-down decay constant $\tau$ is determined by the total RDC losses. For a background or reference measurement performed on an empty cavity, the total losses involve only mirror losses (non-perfect reflectivity, diffraction, etc.). For a cavity containing a sample, which is optionally mounted on or confined by a sample support, additional losses within the cavity include scattering, reflection and/or absorption at the support interfaces (undesirable), and absorption by the sample. The sample support may be a substrate, a closed container for the sample, a container having one, two or more apertures to allow liquid flow into and out of the container, or other suitable apparati that provide at least two substantially parallel interfaces for the sample material. The losses produced by the support can be measured by a frequency scan within the cavity, sans sample. The sample absorption spectrum is then measured by "subtracting" the mirror losses and the support losses from the measured total losses. A sample support may be needed for a liquid, thin film or bulk sold sample and may also be needed for a gas sample that fills only part of the optical cavity C.

In order to preserve the sensitivity of the CRDS technique, losses caused by any sample support within the cavity should be minimized. For any interface between first and second, different, substantially homogeneous materials, an incidence angle can be determined for which a light beam, incident upon the interface at that angle and having a light polarization direction that is parallel to a plane containing the interface, will be transmitted with no reflected component. This incidence angle, $\theta_B$, the Brewster angle for this interface, minimizes or eliminates optical intensity losses due to reflections at the interface. The Brewster angle is determined by the relationship $$\tan\theta_B = n_{ref,2}/n_{ref,1}, \quad (4)$$

where $n_{ref,1}$ and $n_{ref,2}$ are the (real) refractive indices for the first and second media, respectively. See M. Born and E. Wolf, *Principles of Optics*, Pergamon Press, Oxford, Fifth Edition, 1975, pp. 36–44, for a discussion of this relationship. The Brewster angles for water ($n_{ref,2}=1.33$) and for a typical glass ($n_{ref,2}=1.5$), relative to an interface with a vacuum, have the respective values of 53.061° and 56.310°.

The fractional intensity loss in the transmitted component of a p-polarized light beam incident on the interface at an angle $\theta 1 = \theta_B + \delta\theta 1$ is approximately proportional to $\sin^2(\delta\theta 1)$ so that the intra-cavity optical loss in the transmitted component intensity will increase quite rapidly for small, non-zero values of $\delta\theta 1$. This increase in the reflected component intensity, from an ideal value of 0, will reduce CRDS sensitivity and should be minimized, preferably by arranging for the light beam incidence angle to be as close as possible to the Brewster angle $\theta B$. If the sample is a gas that occupies the entire volume of the optical cavity C, or if no sample support is present, or if no sample is present, imposition of the constraint (4) is not necessary.

FIG. 1 illustrates a preferred orientation of a sample 13, optionally associated with a sample support 15, relative to a light beam LB that moves between a first mirror 11-1 and a second mirror 11-2. The mirrors 11-1 and 11-2 have the respective selected mirror radii r1 and r2, have the respective selected reflectivity coefficients R1 and R2, are spaced apart a selected separation distance D facing each other, and define an optical cavity C1. The two-mirror optical resonator defined by the mirrors 11-1 and 11-2 is optically stable only if the parameters r1, r2 and D satisfy the constraints $$0 \leq (1-D/2\cdot r1)(1-D/2\cdot r2) \leq 1, \quad (5)$$

as shown by Yariv, op cit, pp. 18–22. An optically unstable resonator having two mirrors arranged as shown in FIG. 1 will allow a light beam of a selected size to grow without limit and to expand beyond the boundaries of the mirrors.

The light beam LB in FIG. 1 approaches the sample 13 with an incidence angle substantially equal to $\theta_B$ for the light beam wavelength $\lambda$ of interest. A sample support 15 is optionally provided for the sample 13, depending upon the form in which the sample is provided. If the sample 13 is a bulk solid, capable of maintaining its own shape, the sample support 15 may be deleted. If the sample 13 is a thin film, the sample support 15 may be a one-sided or two-sided mechanism that supports and maintains the thin film as a planar surface oriented at an incidence angle $\theta_B$ for the light beam LB. If the sample 13 is a liquid, the sample support 15 may be a container that holds the liquid sample (and, optionally, allows the sample to flow in a selected direction).

Preferably, the portion of the sample support 15 through which the light beam LB passes has a refractive index that is the same as the refractive index for the sample at the frequency $\nu$ used for sample probing. This equality of refractive indices may be achieved only approximately, if a substantial band of frequencies $\nu$ (or corresponding wavelengths $\lambda$) is used for sample probing.

FIG. 2 illustrates an embodiment of a system 21 for practicing the invention to obtain a selected sequence of frequencies within an optical cavity C. Three or more spaced apart optical reflectors ("mirrors"), 23-1, 23-2, 23-3, are configured to form the optical cavity C so that a light beam that travels from a first selected spot or region on a first mirror to a second selected spot or region on a second mirror will be reflected from the second mirror and will ultimately return to the first region on the first mirror, be reflected from the first mirror, and again propagate toward and be reflected from the second region of the second mirror. Alternatively, the cavity C may be defined by two mirrors 11-1 and 11-2, as illustrated in FIG. 1.

In the ring configuration shown in FIG. 2, the cavity C is formed by three or more mirrors, at least one mirror (23-3) having a curvilinear surface rather than a planar surface; the other two mirrors, 23-1 and 23-2, may have planar or curvilinear surfaces. Each of the first, second and third mirrors 23-i (i=1, 2, . . . ) has a reflecting surface with a reflection coefficient $R_i(\theta i, \nu)$ ($\leq 1$) that depends upon the light beam incidence angle $\theta i$ at the mirror i and upon the (narrow band) frequency $\nu$ of the light beam incident thereon, and possibly on other variables as well. Each of the first and second mirrors, 23-1 and 23-2, preferably has a reflection coefficient $R_j(\theta j, \nu)$ (j=1, 2) that is very close to, but not equal to, 1.0, in a preferred range such as $0.99 \leq R_j(\theta j, \nu) \leq 0.9999$. A small fraction of the light beam incident upon mirror no. j will be transmitted through, rather than being reflected from, this mirror. In the embodiment illustrated in FIG. 2, the third mirror 23-3 preferably has a reflection coefficient $R_3(\theta 3, \nu)$ that is as close to 1.0 as possible. The number of mirrors employed here may be two (as in FIG. 1), three (as in FIG. 2), or four or more.

A source 25 of coherent light, such as a visible or infrared laser with a selected narrow range of emission frequencies, provides an initial light beam LB0 that is received by and passed through the first mirror 23-1 and thereafter propagates within the optical cavity along a chosen light beam path LBP. The incidence angle at which the initial light beam LB0 approaches the first mirror 23-1 from the backside is preferably chosen to be approximately equal to the incidence angle $\theta 1$ for the light beam path LB/P at the first mirror 23-1. The light beam source 25 has an associated light beam frequency discrimination device 16 that provides a light beam with a selectable frequency $\nu$ having a line width that $\Delta\nu'$ that is preferably in the range $0.001\text{ cm}^{-1} \leq \Delta\nu' \leq 1\text{ cm}^{-1}$, or smaller if desired. Alternatively, the optical cavity C may have another optical coupling means, such as an acousto-optical or electro-optical modulator, as discussed in U.S. Pat. No. 5,815,277, issued to Zare et al and incorporated by reference herein, to couple the initial light beam LB0 into the cavity in a direction approximately coinciding with the light beam path LBP.

The initial light beam LB0 is passed through a beam polarizer 27 (optional) and through a first cavity coupler 29 that couples the initial light beam into the optical cavity C. The cavity coupler 29 may be merely a selected portion of the back side of the first mirror 23-1 that is specially configured and/or treated to allow a substantial portion (~0.1–2 percent) of the initial light beam LB0 to pass through the first mirror and into the cavity C, or the cavity coupler may be more elaborate. After the light beam enters the cavity C, the light beam follows the light beam path LB/P from one mirror to the next, possibly losing a small amount of its light beam intensity I at each reflection from each mirror 23-i.

The three mirrors, 23-1, 23-2 and 23-3, and the optical cavity C defined by the mirrors, are located within a container 31 whose interior pressure can be controlled, if desired. A sample S, which may be a gas, a liquid or an optically thin solid, is optionally located in a sample region SR of the interior of the container 31 that is intersected by the light beam path LB/P, preferably as indicated in FIG. 2. Each time the light beam passes through the sample region SR, a small fraction of the light beam intensity is absorbed by the molecule(s) contained in the sample S. Optionally, the sample region SR may include all of the optical cavity, or even substantially all of the interior of the container 31. Optionally, the sample S may be deleted; and the optical cavity C may be evacuated and may serve as an optical resonator for one or a sequence of chosen frequencies corresponding to the free spectral range for the resonator.

At a selected one of the mirrors (shown as the second mirror 23-2 in FIG. 2 for definiteness), a selected small fraction of the light beam is extracted from the optical cavity C by a second cavity coupler 33. Preferably, this second small fraction is in the range 0.1–2 percent, but may be smaller or larger if desired. The extracted light defines an extracted light beam LBe that is received by an optional light beam analyzer 35, or by another optional light beam application device 36 that utilizes the light beam for some purpose other than light beam analysis.

The analyzer 35 analyzes the light beam LBe and determines the amount of sample absorption (if a sample is present within the cavity C) and cavity loss, referred to collectively as the total light beam attenuation A, that the light beam intensity has experienced in its peregrinations within the cavity C. The total attenuation A includes a portion due to optical losses $A_{cav}$ arising from beam reflections at each mirror and a residual portion $A_{res}$ due to absorption of the light beam intensity by the sample S. After the attenuation $A=A_{cav} \cdot A_{res}$ has been determined by the analyzer 35 for one or more frequencies ν, the numerical value for the attenuation is visually displayed by an optional visual display module 37 and/or stored in an optional memory module 39 for subsequent use.

The light beam application device 36 may receive and apply the extracted light beam LBe for purposes of spectroscopy, atomic or molecular excitation, absorption measurements on another sample, or any other application that requires provision of a light beam having two or more distinct frequencies.

In a preferred embodiment of the invention, the optical losses and the sample losses, if any, are chosen so that the ring down time τ lies in a selected range, such as 1 μsec<τ≦5 μsec. Assume that the fractional optical losses per round trip and the fractional sample losses per round trip are collectively given by $\exp(-\beta-\alpha \cdot d)$, that the time interval required to complete a round trip in the cavity is $\Delta\tau(\sim c' \cdot d)$, where c' is a representative velocity of the light beam within the cavity) and that the temporal length of the light beam pulse is less than Δτ. The fractional loss, $\exp(-\beta 0)$, and the time increment, Δτ0, required for the light beam to move from its point of insertion in the cavity to its point of extraction (first pass) are assumed to be known. The loss-weighted average time, τ(avg), required for the light beam to emerge from the cavity after the beam's initial insertion is computed as $$\tau(avg) = \sum_{n=0}^{\infty} \exp(-\beta 0) w^n \{\Delta\tau 0 + n \cdot \Delta\tau\}/L0 \qquad (6)$$
$$= \exp(-\beta 0)\{w \cdot \Delta\tau 0 + (1-w) \cdot \Delta\tau\}/L0 \cdot (1-w)^2,$$

$$w = \exp(-\beta - \alpha \cdot d), \qquad (7)$$

$$L0 = \sum_{n=0}^{\infty} w^n = 1/(1-w). \qquad (8)$$

If the loss-weighted average time τ(avg) is set equal to a fraction χ of a desired time τe (e.g., χ=1, 0.5, 0.33, 0.2 or 0.1), the numerical value of the variable w is estimated from Eqs. (6), (7) and (8) by the relation $$\chi \cdot \tau e - \Delta\tau - \Delta\tau 0) \cdot w = \chi \cdot \tau e - \Delta\tau 0, \qquad (9)$$

from which the numerical values for the loss components β and α·d required to produce the desired ring down time τe can be estimated. The sample absorption loss component αx is substantially fixed, but the optical loss coefficient β and/or the round trip distance d can be varied to satisfy Eq. (9). If no absorbing sample is placed in the cavity, a=0.

Figure 3:
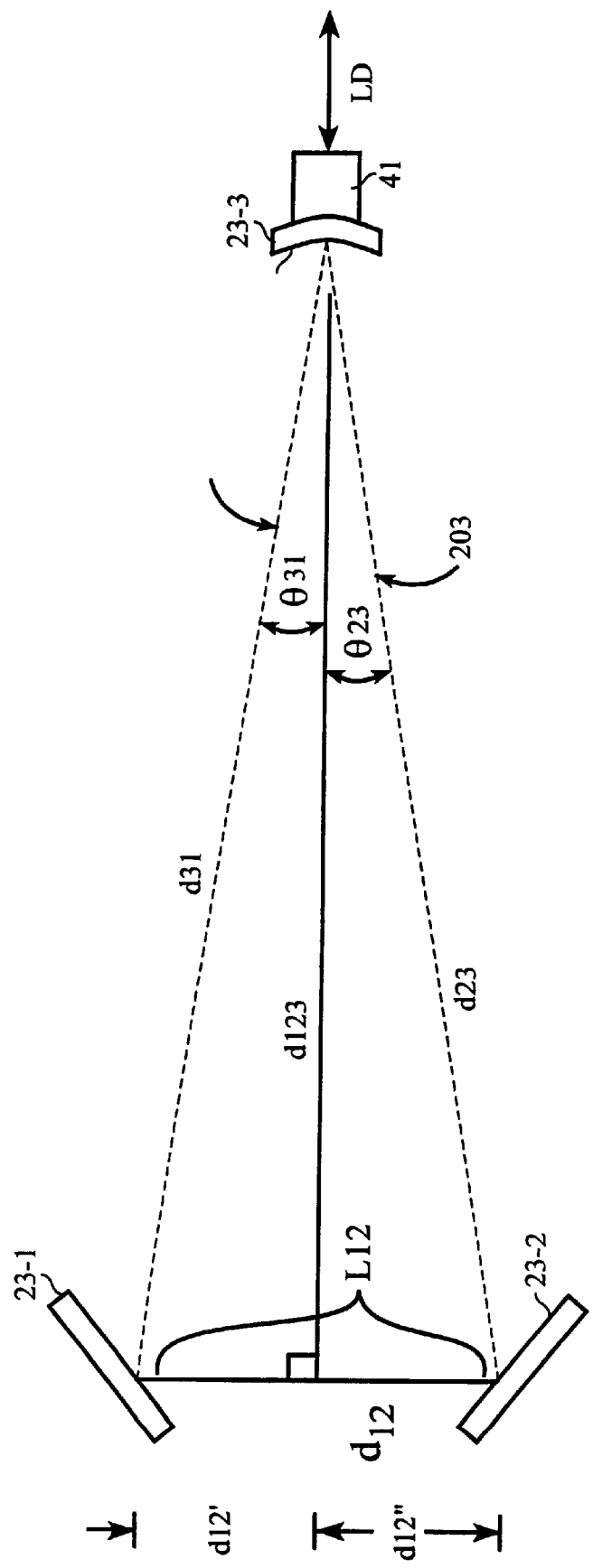

At least one of the mirrors, 23-1, 23-2 and 23-3, shown as 23-3 in FIG. 3, is connected to a displacement control device 41 that controls a perpendicular distance, d123, between a line segment L12 joining the mirrors 23-1 and 23-2 and the mirror 23-3. For convenient reference, the distance d123 is measured perpendicular to the line segment L12 so that the mirror separation distances d23 and d31 are determined by the relations $$d23=d123 \cdot \sec\Theta 23, \qquad (10)$$

$$d31=d123 \cdot \sec\Theta 31, \qquad (11)$$

where Θ23 and Θ31 are angular components for the lght beam reflected at the mirror 23-3. The angular components Θ23 and Θ31 satisfy the constraint $$\Theta 23+\Theta 31=2 \cdot \theta 3, \qquad (12)$$

where θ3 is the incidence angle for the light beam LB at the mirror 23-3.

The displacement control device 41 may be a piezoelectric transducer or any other suitable device that is capable of displacing the mirror 23-3, preferably without rotation, in the LD direction along the line segment L123 by a selected amount Δx (positive or negative). If a sample S with refractive index $n_S$ is present and occupies a fraction, f12, f23 and f31, of the respective distances d12, d23 and d31 for mirror separation in FIG. 3, a light beam having a selected wavelength λ will be resonant within the optical cavity if these distances satisfy a constraint $$\{f12 \cdot d12+f23 \cdot d23+f31 \cdot d31\}/(\lambda/n_S)+\{(1-f12) \cdot d12+(1-f23) \cdot d23+(1-f31) \cdot d31\}/\lambda=N, \qquad (13A)$$

for a refractive index-weighted round trip distance d, where N is a positive integer. If the sample fills the entire cavity, f12=f23=f31=1. If no sample is present, f12=f23=f31=0.

The constraint (9A) can be re-expressed in terms of the distance d123 as $$\{f12 \cdot d12 + f23 \cdot d123 \cdot \sec\Theta 23 + f31 \cdot d123 \cdot \sec\Theta 31\}/(\lambda/n_s) + \{(1-f12) \cdot d12 + (1-f23) \cdot d123 \cdot \sec\Theta 23 + (1-f31) \cdot d123 \cdot \sec\Theta 31\}/\lambda = N \quad (13B)$$

The component angles $\Theta 23$ and $\Theta 31$ can be separately determined as functions of the distance d123, using a tangent relationship for each of the two component triangles shown in FIG. 3:

$$\tan\Theta 23 = d12''/d123, \quad (14A)$$

$$\tan\Theta 31 = d12'/d123, \quad (14B)$$

where d12' and d12'' are the two fixed, complementary components of the mirror separation distance d12 shown in FIG. 3. The value of the trigonometric quantity $\sec\Theta(\Theta = \Theta 23$ or $\Theta 31)$ in the constraint (13B) is determined using the trigonometric relation $$\sec\Theta = \{1 + \tan^2\Theta\}^{1/2}. \quad (15)$$

The relations (14A), (14B) and (15) determine all variable quantities in the wavelength constraint (13A) or (13B) (or corresponding frequency constraint) in terms of the distance value d123 and provide a direct, but nonlinear, relationship between resonance wavelength(s) $\lambda$, the distance d123, and the incidence angles $\Theta 23$ and $\Theta 31$.

The displacement control device 41 is arranged to move to a first distance, d123=d123(1), satisfying the constraint (13A) or (13B) for a first selected frequency $\nu 1$, considered as a first central frequency, and to dither or otherwise vary the distance d123 by a small positive and negative amount for a first time interval given by $t(1) - \Delta t(1) \leq t \leq t(1) + \Delta t(1)$, where $t(1)$ and $\Delta t(1)$ are selected time values. This dithering causes the first central frequency to vary by a small amount around the first selected frequency value, $\nu 1$.

The round trip distance d may be controlled, instead, by providing frequency locking, using techniques such as those discussed by Ahola, Hu and Ikonen, Rev. Sci Instrum., vol. 69 (1998) pp. 1934–1937, and by Shaddock, Gray and McClelland, Optics Lett., vol. 24 (1999) pp. 1499–1501. Whether dithering or frequency locking is used, the refractive index-weighted round trip distance d is stepped through each of a sequence of values corresponding to the desired frequencies within a range for which optical cavity gain, illustrated in FIG. 5, is substantially greater than zero (e.g., equal to at least 10 percent of the gain maximum value).

The displacement control device 41 is arranged to move to a second distance, d123=d123(2), satisfying the constraint (13A) or (13B) for a second selected frequency $\nu 2$, considered as a second central frequency, and to dither or otherwise vary the distance d123 by a small positive and negative amount for a first time interval given by $t(2) - \Delta t(2) \leq t \leq t(2) + \Delta t(2)$, where $t(2)$ and $\Delta t(2)$ are selected time values satisfying $t(1) + \Delta t(1) \leq t2 - \Delta t(2)$. This dithering causes the second central frequency to vary by a small amount around the second selected frequency value, $\nu 2$. Alternatively, frequency locking can be employed, as indicated in the preceding discussion. This procedure continues until each of a selected sequence, $\{\nu k\}(k=1, 2, \ldots)$, of central frequencies is generated within the optical cavity C for a corresponding time interval $t(k) - \Delta t(k) \leq t \leq t(k) + \Delta t(k)$. A representative sequence of central frequencies $\nu k$, with frequency dithering imposed, is illustrated graphically in FIG. 4. Each time interval with a characteristic central frequency $\nu k$ preferably is given a distinguishing identifying indicium $\nu(k)$.

Figure 5:
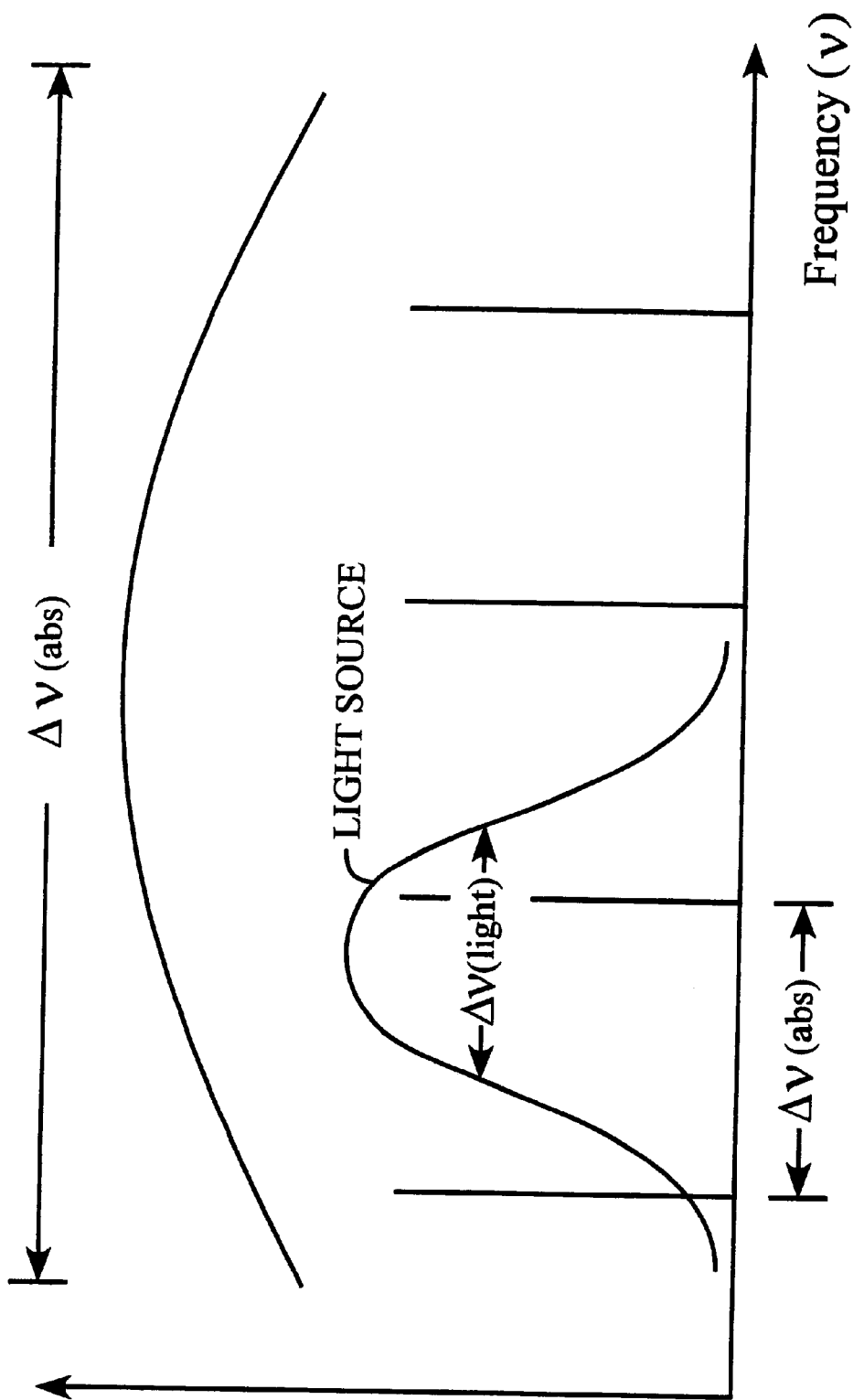
FIG. 5 schematically illustrates a suitable choice of a sequence of central frequencies that can be generated using the invention.

FIG. 5 schematically illustrates a suitable frequency sequence for the invention. Initially, the apparatus is arranged to provide a first resonant frequency sequence $f_{0,1}, f_{0,2}, \ldots, f_{0,M0}$, in a first frequency range that may include a selected first longitudinal mode resonant frequency $f_{TEM(0,0)}$. The apparatus is rearranged to provide a second resonant frequency sequence $f_{1,1}, f_{1,2}, \ldots, f_{1,M1}$, in a second frequency range that may include a selected (not necessarily consecutive) second longitudinal mode resonant frequency $f_{TEM(1,0)}$. Optionally, the apparatus is rearranged to provide a third resonant frequency sequence $f_{2,1}, f_{2,2}, \ldots, f_{2,M2}$, in a third frequency range that may include a selected (not necessarily consecutive) third longitudinal mode resonant frequency $f_{TEM}(2,0)$. This rearrangement of the apparatus is repeated as often as desired.

With reference to FIG. 3, the resonant frequency for a particular configuration of the optical cavity C is inversely proportional to the round trip distance d, and d varies approximately linearly with the displacement distance D, for small incremental displacements $\Delta D$. For relatively large displacement increments $\Delta D$, the relationship between d and D is nonlinear, not linear. For this reason, it is preferable that the optical cavity be changed at least once, from a first longitudinal mode resonant frequency configuration, TEM (m,0), to a second longitudinal mode resonant frequency configuration, TEM(m,0), with m≠n. By limiting the displacement increment $\Delta D$ to a relatively small amount around each TEM(m,0) configuration, a linear relationship between $\Delta D$ and a frequency increment $\Delta f$ can be approximately maintained.

Figure 6:
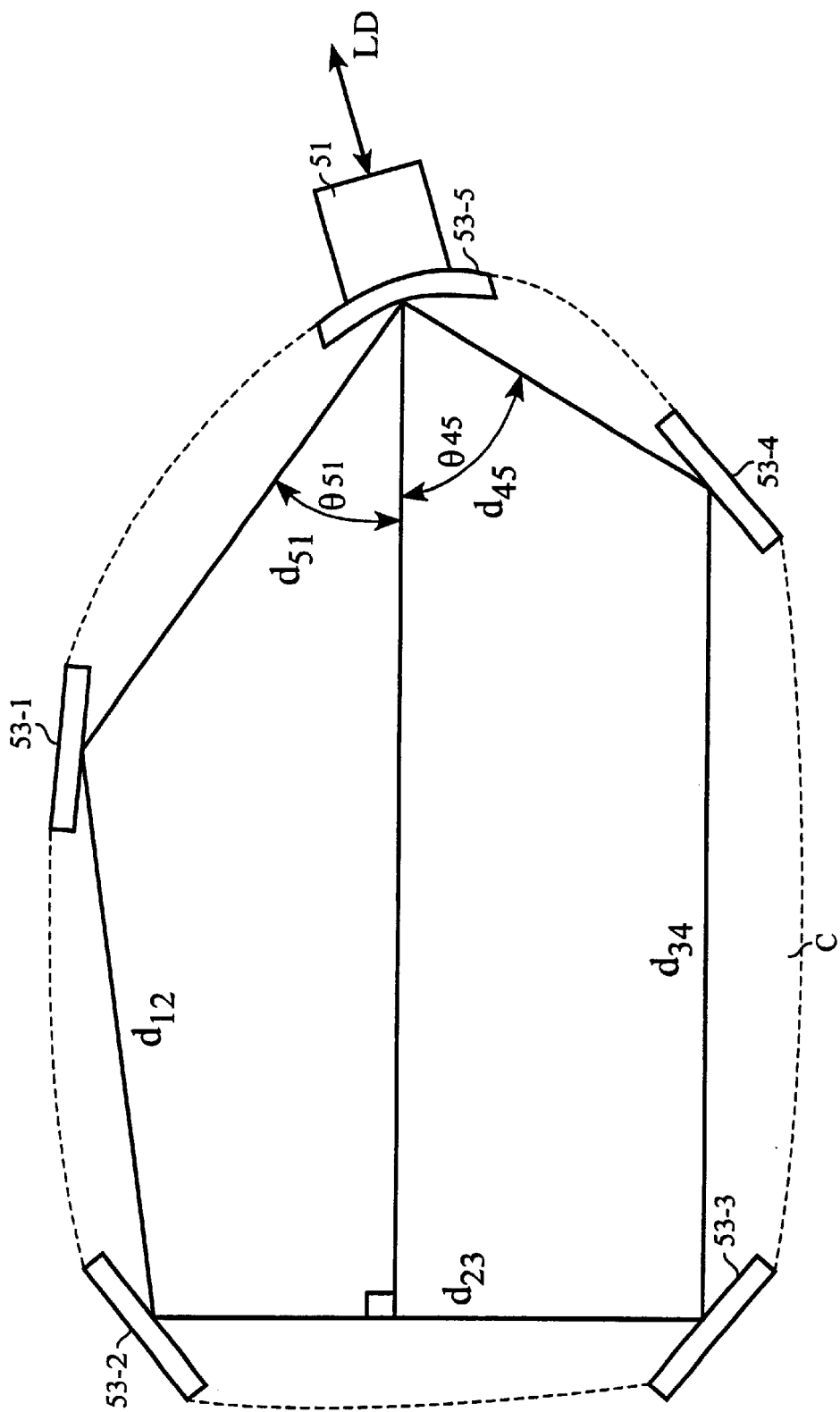
FIG. 6 is a graphic view comparing typical sample absorption, cavity longitudinal modes and light beam components, as a function of frequency.

FIG. 6 is a graphical representation of a typical situation, in which an absorption width, $\Delta \nu(abs)$, of a sample present in the optical cavity C is much greater than the spacing or free spectral range, $\Delta \nu(cav)$, between adjacent longitudinal modes in the cavity, and the (almost monochromatic) light beam has a characteristic range, $\Delta \nu(light)$, of frequencies that may be less than, approximately equal to or greater than the mode spacing $\Delta \nu(cav)$.

Figure 4:
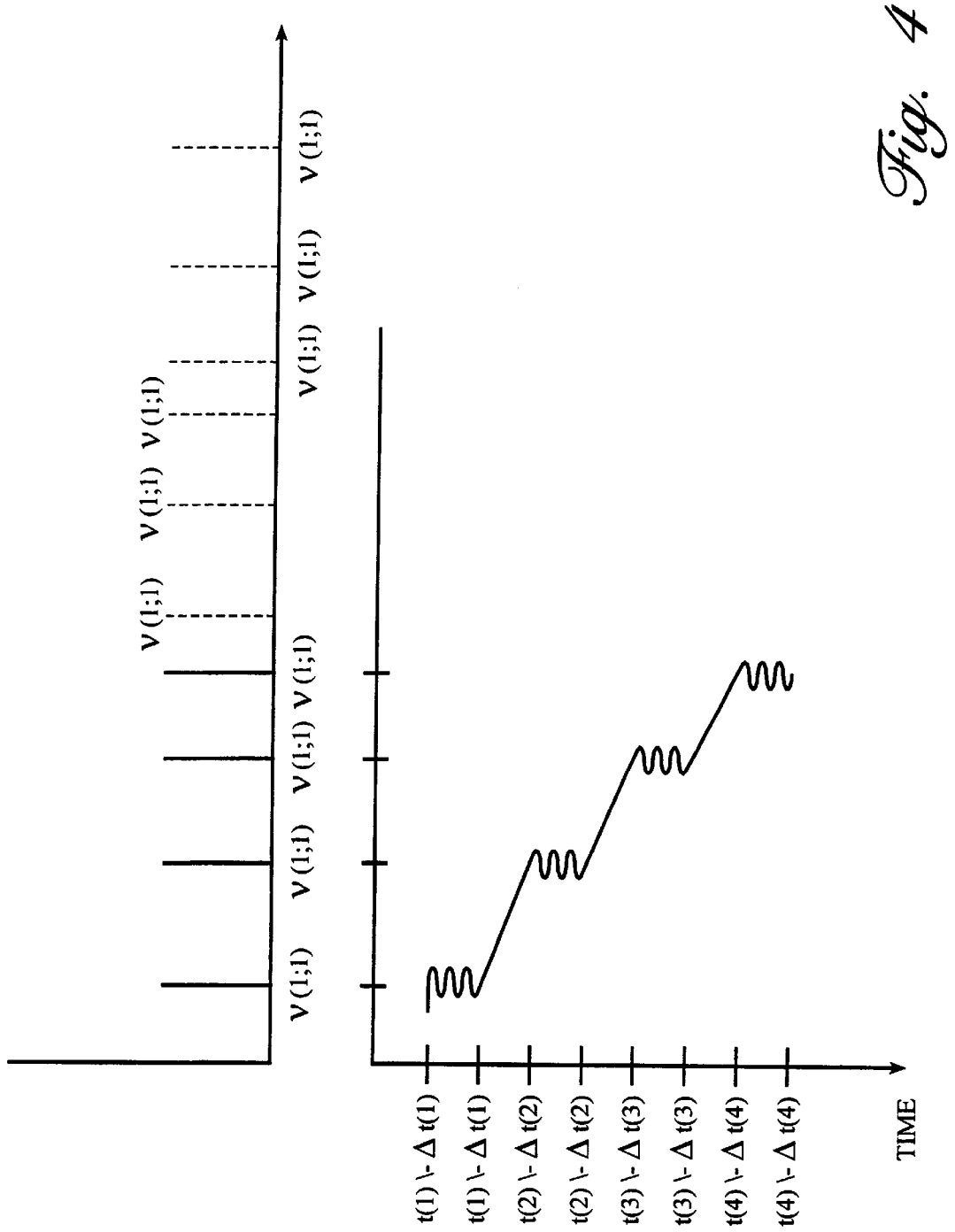
FIG. 4 is a graphic illustration of variation with time of one or more central frequencies associated with the optical cavity according to the invention.

Assume, for definiteness, that the light beam frequency range $\Delta \nu(light)$ is substantially less than the mode spacing so that at most a single longitudinal mode is associated with the optical cavity C, and that the cavity round trip length d=d12+d23+d31 is varied so that the cavity central frequency (favored longitudinal mode) varies with time as shown in FIG. 4. A light beam having a single (dithered) central frequency $\nu k$ is then produced within the cavity, within a given time interval, $t(k) - \Delta t(k) \leq t \leq t(k) + \Delta t(k)$. This sequence of selected frequencies $\nu k$ can be uniformly spaced or non-uniformly spaced, as desired.

If the light beam frequency range $\Delta \nu(light)$ overlaps more than one longitudinal mode so that two or more longitudinal modes (numbered i=1, 2, ... ) are associated with the optical cavity C, a light beam having two or more (dithered) central frequencies, $\nu(i;k)$ is then produced within the cavity, within a given time interval, $t(k) - \Delta t(k) \leq t \leq t(k) + \Delta t(k)$, as illustrated in FIG. 4.

If the arrangement shown in FIG. 2, having two or more mirrors, is to be used for CRDS analysis, a sample S is positioned within part or all of the optical cavity C, and the extracted light beam LBe is received by the light beam analyzer 35, to construct an absorption spectrum or transmission spectrum for the sample.

If the arrangement shown in FIG. 2 is to be used to provide a selected sequence of central frequencies $\nu k$ (with or without frequency dithering) for a purpose other than CRDS, the extracted light beam LBe is received by some other light utilization device 36 and is processed accordingly. The preceding analysis can be extended to a two-mirror optical cavity, as shown in FIG. 1, by an analogous development. The preceding analysis can also be extended to a polygonal cavity, as shown in FIG. 7, where a sequence of mirrors 53-i (i=1, 2, 3, 4, ... ) defines an optical cavity C.

Where frequency locking, rather than frequency dithering, is used in connection with each of a sequence of selected frequencies, the frequency lock will occur in each of a sequence of time intervals, separated by lock-off time intervals with lengths typically $\Delta t(off) \sim 5-100$ μsec. Until frequency lock is achieved at a selected central frequency, the initial light beam LB0 is FIG. 2 is preferably not admitted into the cavity C, in order to ensure that the light beam propagates within the cavity having a known resonant configuration. Alternatively, the initial light beam LB0 can be admitted into the cavity C when frequency lock has not yet been achieved, but the extracted light beam LBe can be diverted, absorbed or otherwise blocked until frequency lock has been achieved at a selected central frequency.

Where a sample S is positioned within the optical cavity C, the extracted light beam LBe will have a selected resonant frequency and a characteristic ring down time $\tau(S)$ that depends upon the optical losses at each mirror, upon the optical losses for beam insertion and beam extraction, and upon the sample absorption within the cavity. Where no sample ("S=S0") is positioned within the (same) optical cavity C, the extracted light beam LBe will have a selected resonant frequency and a characteristic ring down time $\tau(S0)$ that depends upon the optical losses at each mirror and upon the optical losses for beam insertion and beam extraction, with $\tau(S0) > \tau(S)$.

Where an initial light beam LB0 of finite temporal length is generated and inserted into the cavity C, the intensity of the extracted light beam LBe will increase to a plateau value, then decrease monotonically after the tail of the light beam has entered the cavity, with a characteristic ring down time $\tau$ for the light beam portion with decreasing intensity. Where an initial light beam with unlimited temporal length is generated and inserted into the cavity c, the intensity of the extracted light beam will increase to an intensity plateau value that includes the effects of light beam insertion, round trip sample absorption losses (if any) and optical losses, and light beam extraction.

What is claimed is:

1. A method for providing a light beam having a sequence of two or more selected frequencies, the method comprising:
    providing an optical cavity, defined by at least first and second spaced apart mirrors, where the first mirror is movable relative to the second mirror to provide at least a first cavity configuration and a second cavity configuration corresponding to a selected first cavity frequency and a selected second cavity frequency, respectively;
    introducing a light beam, having a selected narrow frequency band, into the optical cavity arranged in the first cavity configuration and varying a distance of the first mirror from the second mirror, to produce a first light beam having the first cavity frequency;
    introducing the light beam into the optical cavity arranged in the second cavity configuration and varying a distance of the first mirror from the second mirror, to produce a second light beam having the second cavity frequency;
    positioning a sample of selected material within a selected portion of the cavity;
    sequentially allowing the first light beam and the second light beam to pass through the sample;
    sequentially extracting the first light beam and the second light beam from the cavity, after the first light beam and the second light beam have passed through the sample;
    analyzing said extracted first light beam and the extracted second light beam to determine absorption of the light beam at the first cavity frequency and at the second cavity frequency by the sample;
    choosing the sample absorption so that substantially all of at least one of the first light beam and the second light beam is extracted from the cavity within a selected time interval; and
    choosing round trip fractional sample absorption loss, $\alpha \cdot d$, and round trip fractional optical loss, $\beta$, in the cavity to approximately satisfy a relation $$(\tau e - \Delta \tau - \Delta \tau 0) \cdot \exp(-\beta - \alpha \cdot d) = \tau e - \Delta \tau 0,$$

where $\Delta \tau$ is an estimated time interval for light beam round trip in the cavity, $\Delta \tau 0$ is a selected fraction of $\Delta \tau$ and $\tau e$ is the selected time interval for extraction of the light beam from the cavity.

2. The method of claim 1, further comprising producing at least one of said first and second cavity frequencies by frequency locking.

3. The method of claim 1, further comprising providing at least one of said first cavity frequency and said second cavity frequency as a dithered frequency about a selected central frequency.

4. The method of claim 1, further comprising choosing said light beam introduced into said cavity to have a light beam frequency width that is substantially less than spacing between two adjacent longitudinal mode resonant frequencies for said cavity.

5. The method of claim 1, further comprising choosing said light beam introduced into said cavity to have a light beam frequency width that is at least equal to spacing between two adjacent longitudinal mode resonant frequencies for said cavity.

6. The method of claim 1, further comprising choosing said selected narrow frequency band of said light beam to lie in a range given by $0.001 \text{ cm}^{-1} \leq \Delta v' \leq 1 \text{ cm}^{-1}$.

7. A method for providing a light beam having a sequence of two or more selected frequencies, the method comprising:
    providing an optical cavity, defined by at least first and second spaced apart mirrors, where the first mirror is movable relative to the second mirror to provide at least a first cavity configuration and a second cavity configuration corresponding to a selected first cavity frequency and a selected second cavity frequency, respectively;
    introducing a light beam, having a selected narrow frequency band, into the optical cavity arranged in the first cavity configuration and varying a distance of the first mirror from the second mirror, to produce a first light beam having the first cavity frequency;
    introducing the light beam into the optical cavity arranged in the second cavity configuration and varying a distance of the first mirror from the second mirror, to produce a second light beam having the second cavity frequency;
    sequentially extracting the first light beam and the second light beam from said cavity to provide first and second extracted light beams having the first cavity frequency and the second cavity frequency, respectively;
    choosing mirror reflectivity for at least one of the first and second mirrors so that substantially all of at least one of the first light beam and the second light beam is extracted from the cavity within a selected time interval; and
    choosing round trip fractional optical loss, $\beta$, in the cavity to approximately satisfy a relation $$(\chi \cdot \tau e - \Delta \tau - \Delta \tau 0) \cdot \exp(-\beta) = \chi \cdot \tau e - \Delta \tau 0,$$

where $\Delta\tau$ is an estimated time interval for light beam round trip in the cavity, $\Delta\tau 0$ is a selected fraction of $\Delta\tau$, $\tau e$ is the selected time interval for extraction of the light beam from the cavity and $\chi$ is a selected fraction in a range $0.1 \leq \chi \leq 1$.

8. The method of claim 7, further comprising choosing said first cavity configuration and said second cavity configuration so that said first cavity frequency and said second cavity frequency are adjacent to a selected first longitudinal mode resonant frequency and to a selected second longitudinal mode resonant frequency, respectively.

9. The method of claim 8, further comprising choosing said first longitudinal mode resonant frequency to be different from said second longitudinal mode resonant frequency.

10. A system for providing as light beam having a sequence of two or more selected frequencies, the system comprising:

an optical cavity, defined by at least first and second spaced apart mirrors, where the first mirror is movable relative to the second mirror to provide at least a first cavity configuration and a second cavity configuration corresponding to a selected first cavity frequency and a selected second cavity frequency, respectively;

a light beam control mechanism for introducing a light beam, having a selected narrow frequency band, into the optical cavity arranged in the first cavity configuration and for varying a distance of the first mirror from the second mirror to produce a first light beam having the first cavity frequency, and for introducing the light beam into the optical cavity arranged in the second cavity configuration and for varying a distance of the first mirror from the second mirror to produce a second light beam having the second cavity frequency;

a light beam analyzer to receive and analyze the extracted first light beam and the extracted second light beam to determine absorption of the light beam at the first cavity frequency and at the second cavity frequency by the sample;

wherein the sample is chosen so that substantially all of at least one of the first light beam and the second light beam is extracted from the cavity within a selected time interval; and choosing round trip fractional sample absorption loss, $\alpha \cdot d$, and round trip fractional optical loss, $\beta$, in the cavity to approximately satisfy a relation $$(\chi \cdot \tau e - \Delta \tau - \tau 0) \cdot \exp(-\beta - \alpha \cdot d) = \chi \cdot \tau e - \Delta \tau 0,$$

where $\Delta\tau$ is an estimated time interval for light beam round trip in the cavity, $\Delta\tau 0$ is a selected fraction of $\Delta\tau$, $\tau e$ is the selected time interval for extraction of the light beam from the cavity and $\chi$ is a selected fraction in a range $0.1 \leq \chi \leq 1$.

11. The system of claim 10, wherein said light beam control mechanism produces at least one of said first and second cavity frequencies by frequency locking.

12. The system of claim 10, wherein said light beam control mechanism produces at least one of said first cavity frequency and said second cavity frequency as a dithered frequency about a selected central frequency.

13. The system of claim 10, wherein:

a sample of selected material is positioned within a selected portion of said cavity;

said first light beam and said second light beam are allowed to sequentially pass through the sample; and said first light beam and said second light beam are sequentially extracted from said cavity by said light beam control mechanism, after said first light beam and said second light beam have passed through the sample.

14. The system of claim 10, wherein said first cavity configuration and said second cavity configuration are chosen so that said first cavity frequency and said second cavity frequency are adjacent to a selected first longitudinal mode resonant frequency and to a selected second longitudinal mode resonant frequency, respectively.

15. The system of claim 14, wherein said first longitudinal mode resonant frequency is chosen to be different from said second longitudinal mode resonant frequency.

16. The system of claim 10, wherein said light beam introduced into said cavity is arranged to have a light beam frequency width that is substantially less than spacing between two adjacent longitudinal mode frequencies for said cavity.

17. The system of claim 10, wherein said light beam introduced into said cavity is arranged to have a light beam frequency width that is at least equal to spacing between two adjacent longitudinal mode frequencies for said cavity.

18. The system of claim 10, wherein said selected narrow frequency band of said light beam is chosen to lie in a range given by $0.001 \text{ cm}^{-1} \leq \Delta v' \leq 1 \text{ cm}^{-1}$.

19. A system for providing as light beam having a sequence of two or more selected frequencies, the system comprising:

an optical cavity, defined by at least first and second spaced apart mirrors, where the first mirror is movable relative to the second mirror to provide at least a first cavity configuration and a second cavity configuration corresponding to a selected first cavity frequency and a selected second cavity frequency, respectively;

a light beam control mechanism for introducing a light beam, having a selected narrow frequency band, into the optical cavity arranged in the first cavity configuration and for varying a distance of the first mirror from the second mirror to produce a first light beam having the first cavity frequency, and for introducing the light beam into the optical cavity arranged in the second cavity configuration and for varying a distance of the first mirror from the second mirror to produce a second light beam having the second cavity frequency;

wherein said light beam control mechanism sequentially extracts the first light beam and the second light beam from said cavity to provide first and second extracted light beams having the first cavity frequency and the second cavity frequency, respectively;

wherein said mirror reflectivity of at least one of the first and second mirrors is chosen so that substantially all of at least one of the first light beam and the second light beam is extracted from the cavity within a selected time interval; and wherein round trip fractional optical loss, $\beta$, in the cavity is chosen to approximately satisfy a relation $$\chi \cdot \tau e - \Delta \tau - \Delta \tau 0) \cdot \exp(-\beta) = \chi \cdot \tau e - \Delta \tau 0,$$

where $\Delta\tau$ is an estimated time interval for light beam round trip in the cavity, $\Delta\tau 0$ is a selected fraction of $\Delta\tau$, $\tau e$ is the selected time interval for extraction of the light beam from the cavity and $\chi$ is a selected fraction in a range $0.1 \leq \chi \leq 1$.

\* \* \* \* \*